United States Patent
Chikami

Patent Number: 5,811,366
Date of Patent: Sep. 22, 1998

[54] FINGERPRINT IMAGE GENERATING METHOD AND FINGERPRINT IMAGE RECORDING SHEET

[75] Inventor: Nozomu Chikami, Shizuoka, Japan

[73] Assignee: Fuji Photo Film Co., Inc., Kanagawa, Japan

[21] Appl. No.: 641,651

[22] Filed: May 1, 1996

[30] Foreign Application Priority Data

May 1, 1995 [JP] Japan .................................... 7-128769

[51] Int. Cl.⁶ ................................................. B41M 5/165
[52] U.S. Cl. ........................................... 503/201; 503/226
[58] Field of Search .................................... 427/150–152; 503/201, 206, 226

[56] References Cited

U.S. PATENT DOCUMENTS

| | | | |
|---|---|---|---|
| 4,232,083 | 11/1980 | Buerkley et al. | 428/307 |
| 4,879,134 | 11/1989 | Vassiliades | 427/1 |
| 4,903,991 | 2/1990 | Wright | 283/95 |
| 4,960,749 | 10/1990 | Miura et al. | 503/213 |

OTHER PUBLICATIONS

Patent Abstracts of Japan, vol. 5, No. 61 (M–065), Apr. 24, 1981, & JP–A–56 015392 (Fuji Photo Film Co., Ltd.), Feb. 14, 1981, *abstract.

Primary Examiner—Bruce H. Hess
Attorney, Agent, or Firm—Sughrue, Mion, Zinn, Macpeak & Seas, PLLC

[57] ABSTRACT

A fingerprint image generating method and a fingerprint image recording sheet are provided which can take a clear fingerprint image easily and efficiently, without the process of wiping seal ink, with less chance to generate an unclear fingerprint image even in improper operation. A solution containing an electron-donating dye precursor is applied to a fingerprint face of a fingertip and then the fingertip is pressed against a recording film to which an electron-accepting color developer is applied. The electron-accepting color developer adsorbs the electron-accepting dye precursor to occur a coloring reaction on the recording film. The fingerprint image recording sheet includes a fingerprint image recording portion applying the electron-accepting color developer thereto and the electron-donating dye precursor applied portion to which the solution of the electron-donating dye precursor is applied. The solution containing the electron-donating dye precursor is preferably microencapsulated and applied to the support. It is preferable to form the microcapsules to be ruptured merely by rubbing it lightly with the fingertip.

1 Claim, 4 Drawing Sheets

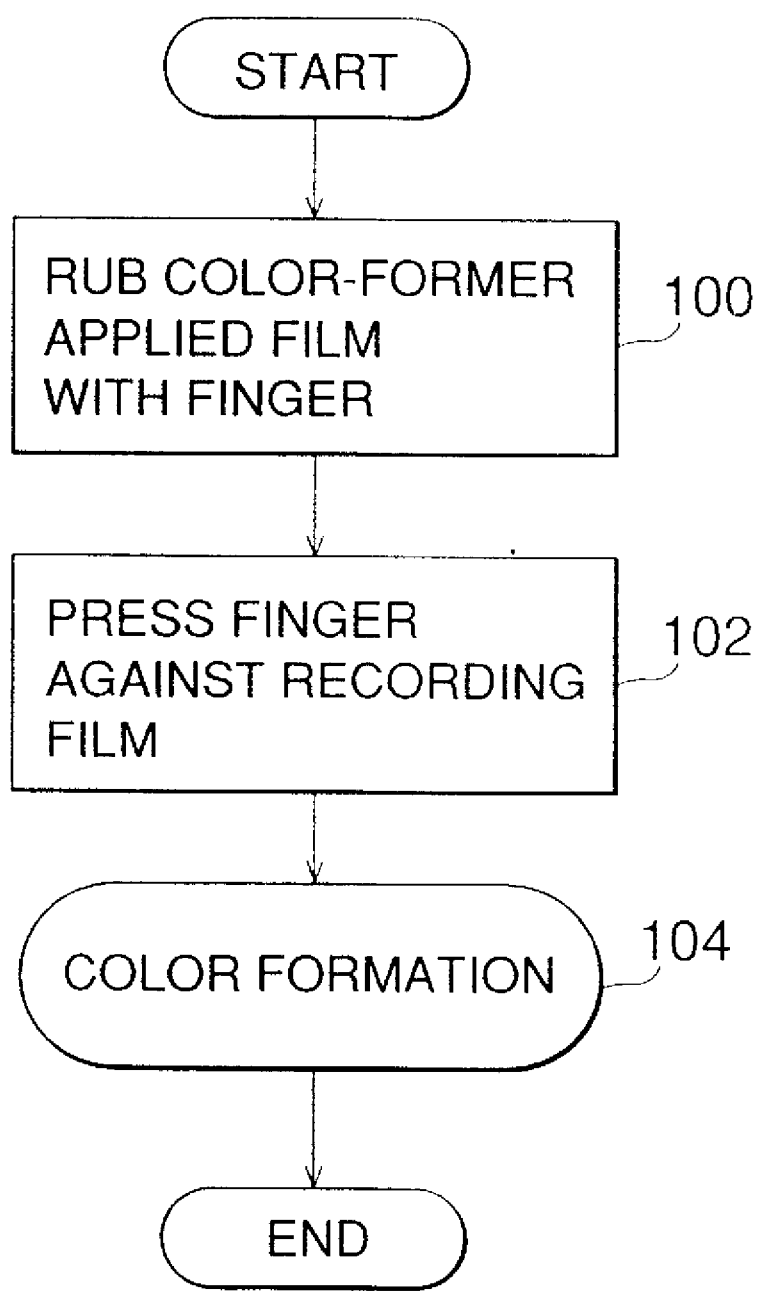

FIG.3A
NORMAL IMAGE
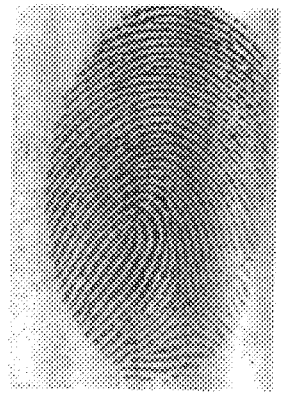
ROTATED IMAGE
FIG.3B
PRIOR ART
NORMAL IMAGE
ROTATED IMAGE

FINGERPRINT IMAGE GENERATING METHOD AND FINGERPRINT IMAGE RECORDING SHEET

BACKGROUND OF THE INVENTION

1. Field of the Invention

This invention relates to a fingerprint image generating method in which a rising streamline patterned image on a fingerprint face of a fingertip is generated with a transferring technique and to a fingerprint image recording sheet practically which may be employed for the fingerprint image generating method.

2. Related Art

Fingerprints have been used as means for identifying a person, for example, in a field of the judicial office for identifying a suspect of a violation of traffic regulations or a criminal.

Conventionally, such fingerprints (fingerprint images) have been taken in the following manner that the fingerprint face of the fingertip is pressed against black seal ink so that the seal ink can adhere to the fingerprint face, and then pressed against a recording sheet. In other words, the seal ink adheres to a projecting portion (also referred as to a rising streamline) on the fingerprint face which has an uneven pattern so that the pattern of the projecting portion (rising streamline) can be transferred to the recording sheet, thus obtaining the rising streamline patterned image of the fingerprint.

In such a conventional method, the black seal ink remained on the fingertip after taking of fingerprint image needs wiping with a tissue paper or a cloth, but it is too difficult to wipe off because the seal ink filled in hollow portions of the uneven pattern on the fingerprint face can not be easily wiped away. Further, the tissue or the cloth needs preparing for wiping the seal ink and disposing thereof after end operation of wiping, resulting in an increase of incidental work.

On the other hand, the recording sheet to which the seal ink is transferred can not be piled up with other documents until the transferred ink dries or unless the wet and excess ink is removed by pressing with a blotter. For this reason, another problem arises that workability is lowered due to time needed for drying the seal ink after taking the fingerprint. Further, in this method, the image of the rising streamline becomes so bold as to lose the pattern thereof when the seal ink is used to excess for application to the fingerprint face, so that a clear fingerprint image can not be obtained.

Furthermore, when performing improper operation such as to press the fingerprint face excessively against the recording sheet or to slightly move the fingertip while pressing it against the recording sheet, the clear rising streamline patterned image of the fingerprint cannot be clearly obtained as well. Thus, it is impossible to make a judgment on finely distinct fingerprint patterns not only in visual inspection, but also in a computing process after reading the fingerprint with a fingerprint reader.

SUMMARY OF THE INVENTION

The present invention has been accomplished under the circumstances as aforementioned, and an object thereof is to provide a method to generate or record a fingerprint image, which can save the trouble of doing after taking the fingerprint such as to wipe seal ink, so that a clear fingerprint image can be obtained easily and efficiently with less chance to generate an unclear fingerprint image even in improper operation.

Another object of the present invention is to provide a recording sheet which may be employed for one embodiment of the above method.

The former object of the present invention is attained by the provision of a method of generating a fingerprint image comprising steps of applying solution to a fingerprint face of a fingertip, the solution containing an electron-donating dye precursor dissolved therein; and pressing the fingertip against a recording film to which an electron-accepting color developer is applied so that the electron-donating dye precursor is adsorbed by the electron-accepting color developer to occur a coloring reaction therebetween on the recording film.

In the present invention, it is preferable to apply microencapsulated solution to a support so that the solution is applied to the fingerprint face by rubbing the solution-applied surface on the support with the fingerprint face of the fingertip. In this case, the microcapsules can be preferably ruptured upon application of pressure of approximately 0.2 to 0.6 MPa, that is, can be ruptured merely by rubbing the solution applied surface lightly with the fingertip.

Then, the amount of oil to adhere to the fingertip is set most preferably so that the amount of the solution to be transferred to the recording film by pressing the fingertip against the recording film falls in a range of 20 to 100 $\mu g/cm^2$.

The latter object of the present invention is attained by the provision of a fingerprint image recording sheet comprising:

- a fingerprint image recording portion to which an electron-accepting color developer is applied; and
- an electron-donating dye precursor applied portion to which a solution of an electron-donating dye precursor is applied, the electron-accepting color developer being capable to adsorb the electron-donating dye precursor to occur a coloring reaction on the fingerprint image recording portion.

It will be understood that the electron-donating dye precursor may be microencapsulated and applied. The fingerprint-image recording portion and the electron-donating dye precursor applied portion can be formed in different regions adjacent to each other. Further, the above two portions may be provided in different positions on the recording sheet such as forth and back faces, or in different pages. In these cases, if the fingerprint-image recording portion is covered with a light-shielding film capable of opening and closing, aged changes or color fading on the recording portion can be prevented.

Furthermore, the electron-donating dye precursor applied portion may be formed on the film covering the fingerprint image recording portion. In this arrangement, the covering film is opened or removed when taking a fingerprint so that the fingerprint face can be pressed against the thus bared recording portion usually covered with the film. After that, the recording portion is closed or covered with the film again. The covering film may be a light-shielding type the upper face of which is coated with the electron-donating dye precursor.

BRIEF DESCRIPTION OF THE DRAWINGS

These and other objects and advantages and further description will now be discussed in connection with the drawings in which:

FIG. 2 is a flow chart showing processing steps of the method;

FIGS. 3A and 3B are diagrams showing comparison between enlarged fingerprint images respectively formed according to the present method and a conventional method.

DETAILED DESCRIPTION OF THE PREFERRED EMBODIMENTS

Figure 1:
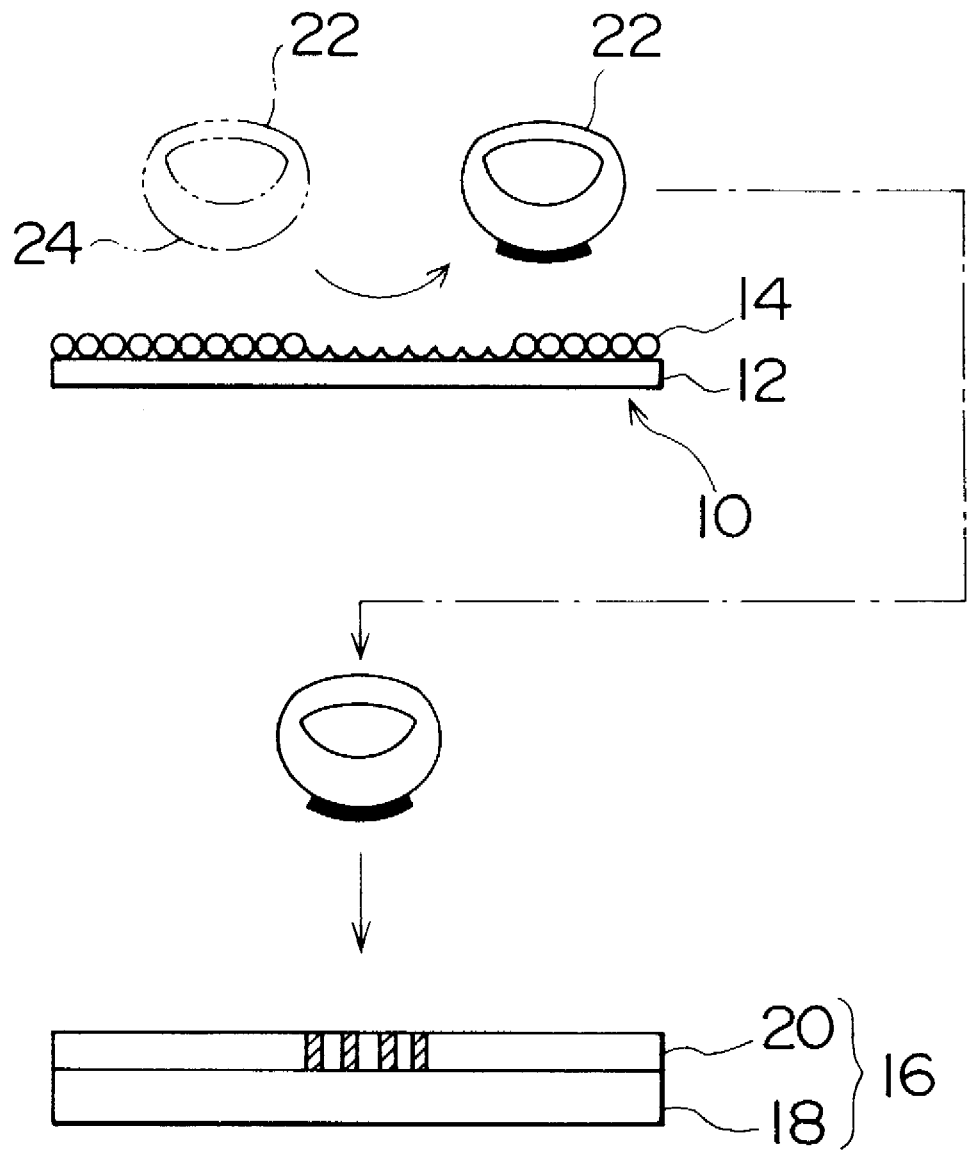
FIG. 1 is a descriptive diagram showing a general idea of a method according to the present invention.

In FIG. 1, a reference numeral 10 denotes an electron-donating dye precursor applied film (hereinafter, also referred as to a color-former applied film), which comprises a support sheet 12 and a microcapsule layer 14. The microcapsule layer 14 is formed on an upper face of the support 12 with an electron-donating dye precursor (hereinafter, also referred as to a color former) in a microcapsulated condition. The support 12 may be made of a plastic film, a metal foil, a resin coated paper or a synthetic paper. The microcapsule layer 14 is formed by applying a microencapsulated solution of the color former in an oil.

The color former is a colorless compound which develops some color upon contact with an electron-accepting color developer (hereinafter, also referred as to a color developer). The color developer is a solid acid, more specifically an electron-accepting solid acid. The color formers and color developers are well known in the art. More detailed description of microcapsules, color formers and color developers which may be used in this invention will be found, for example, in Japanese Patent Publication Nos. 57-24852 (corresponding U.S. Pat. No. 4,002,060) and 59-16654 (corresponding U.S. Pat. No. 4,132,112). The descriptions in the specification of these prior patents will be incorporated herein as the references.

The color former is dissolved in an oil. The oil used herein is also disclosed in the above documents, for example, synthetic oil or natural oil can be used. The solution of the color former is microencapsulated with a known microencapsulation technique, for example, disclosed in U.S. Pat. Nos. 4,002,060 and 4,132,112. As such techniques, coacervation, surface polymerization, internal polymerization and external polymerization are cited.

The microencapsulated color former solution (microcapsule contained solution) is a capsule dispersed solution, so that it can be applied to the support 12 as it is for forming the microcapsule layer 14. It is noted hereby that the microcapsules are regulated to have a strength or resistance as to be easily ruptured when rubbed with a fingertip, preferably to be able to be ruptured upon application of pressure of approximately 0.2 to 0.6 MPa (MPa: megapascal, 1 MPa≈10.2 kgf/m$^2$).

In FIG. 1, a reference numeral 16 denotes a recording film constituted of a support 18 and a layer containing an electron-accepting color developer (hereinbelow, simply referred as to a color developer) 20. The support 18 used herein may be the same as the support 12 used in the color-former applied film 10. The color developer may be either an inorganic solid acid or an organic compound. Such color developers are disclosed in the aforementioned prior art documents. As the color-former applied film 10 and the recording film 16, a pressure measuring system "PRESCALE" (trade name) for ultra-super-low pressure, commercially available from FUJI PHOTO FILM CO., LTD. can be used.

The color-former applied film 10 and the recording film 16 mentioned above are prepared and used for taking a fingerprint image through the following processing steps. First, a fingerprint face 24 of a fingertip 22 (FIG. 1) is put into contact with the microcapsule layer 14 on the color-former applied film 10 so that the microcapsule layer 14 is rubbed therewith (step 100 in FIG. 2). Consequently, the microcapsules in the microcapsule layer 14 are ruptured so that the solution of the color former sealed in the microcapsules adheres to the fingerprint face 24. The fingertip 22 to which the color former solution adheres is then pressed against the color-developer layer 20 on the recording film 16 (step 102), so that the solution of the color former adhering to the fingertip is transferred to the color-developer layer 20, and so that the color former contained in the ruptured capsules is adsorbed together with the oil solution by the color developer to develop a color, red in the illustrated embodiment (step 104).

The solution containing the color former may be colorless and transparent, so that the fingertip hardly shows dirt even in applying the solution thereto. Also, the amount of solution to be applied to the fingertip is remarkably reduced, so that almost all the solution on the fingerprint face of the fingertip is transferred to the recording film 16.

Accordingly, the solution containing the color former hardly remains at the fingertip, if a small amount of solution stays, the remaining solution can be easily removed. In addition, the recording film 16 does not need drying after color formation since the coloring reaction between the color former and the color developer complete instantly.

FIG. 3A shows enlarged fingerprint images formed according to the embodiment of the present invention in which the microcapsule solution is used for applying the color former to the fingerprint face of the fingertip; FIG. 3B shows enlarged fingerprint images formed according to the prior method using the conventional seal ink. In FIGS. 3A and 3B, the left images indicate fingerprint images taken in a normal state that the fingertip was pressed correctly, whereas the right images indicate fingerprint images taken in an improperly operated state such that the fingertip was rotated by a degree of about 45° to the counter-clockwise direction while pressing it against the recording film. Although pressurized portions become red in the pressure measuring system "PRESCALE" (trade name), they may be colored with other color such as black.

As apparent from comparison between FIGS. 3A and 3B, the fingerprint images formed according to the present invention (FIG. 3A) are clearer than those formed using seal ink according to the conventional method (FIG. 3B). It should be noted that there is less blurring in the present invention even in rotated image. This is because the coloring reaction between the color former and the color developer occurs and completes instantly such that the color former completely reacts to the color developer at the moment when contacting first with the color developer, and unreacted color former does not remain on the fingerprint face of the fingertip. For this reason, there will occur no fingerprint image after the first coloring reaction even if the fingertip is pressed anywhere else on the recording film 16.

Figure 4A:
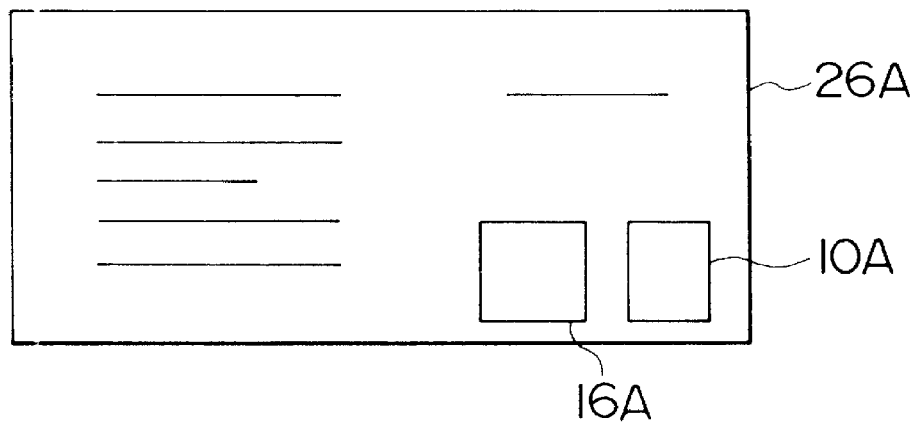
FIGS. 4A, 4B and 4C are diagrams showing embodiments to which the present invention is applied.

Several types of systems are possible to carry out the present invention. For example, as shown in FIG. 4A, a recording sheet 26A according to the present invention can include an electron-donating dye precursor applied portion (hereinbelow, referred as to a color-former applied portion) 10A which puts a color-former applied film 10 thereon, and a fingerprint image recording portion 16A which puts a recording film 16 thereon, the portions arranged adjacent to each other in places on the recording sheet 26A. In this embodiment, a fingertip is rubbed against the color-former applied portion 10A and then pressed against the fingerprint image recording portion 16A, thus generating a fingerprint image in such an easy manner.

Figure 4B:
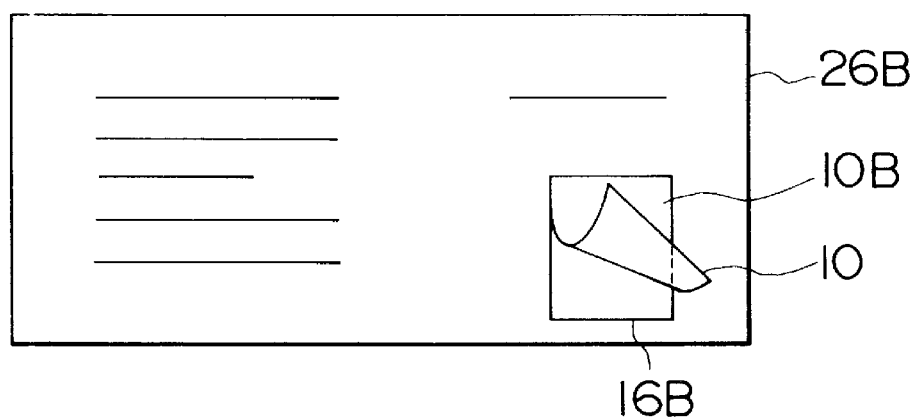

A recording sheet 26B shown in FIG. 4B is constituted such that the color-former applied film 10 is overlaid removably on a fingerprint image recording portion 16B. It should be noted that a color-former applied portion 10B is formed on the upper face of the color-former applied film 10 so that the color-former applied portion 10B can be prevented from contacting with the color developer. In this embodiment, the fingertip is rubbed against the upper face of the film 10 and then pressed against the recording film 16 after tearing the film 10 off. The removed film 10 is a disposable item.

Figure 4C:
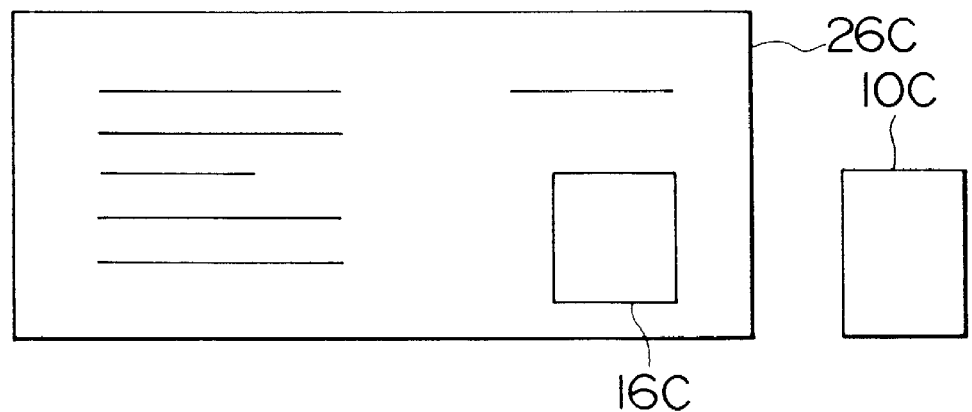

Next, a recording sheet 26C shown in FIG. 4C is consconstituted such that a fingerprint image recording portion 16C is formed on the recording sheet 26C, but a color-former applied film 10 shown as a reference numeral 10C is provided separately from the recording sheet 26C. The recording sheets shown in FIGS. 4B and 4C each have advantage of making a recording area wide.

Further, the recording portions 16A, 16B and 16C may be each covered with a light-shielding film, so that the fingerprint image recorded on the recording portion 16A, 16B or 16C can be prevented from changing or losing color, thereby extending a preservation period of the fingerprint image.

The light-shielding film to be used for the recording sheet in FIG. 4A or 4C can be overlaid on the upper face of the recording portion 16A or 16C. For example, the light-shielding film is bonded to the upper end of the recording portion 16A or 16C so that the recording portion 16A or 16C can be exposed by rolling up the light-shielding film during taking a fingerprint. Alternatively, the light-shielding film may be provided separately from the recording sheet 26A, 26C for covering the recording portion 16A or 16C therewith after taking the fingerprint so that the fingerprint image can be fixed.

In the embodiment shown in FIG. 4B, the support 12 of the color-former applied film 10 can be preformed with a light-shielding film. In this case, the film 10 remains on the recording sheet 26B to keep the recording portion 16B covered therewith.

In the above embodiments, although the color former is microencapsulated after dissolved in oil, the present invention can be applied to a case that the solution of the color former in the oil is used as it is without microencapsulation. In this case, the color former solution may be soaked up with a sponge or a cloth and, when taking a fingerprint, the fingertip is put into contact with the sponge or the cloth into which the solution is soaked so that the solution can be applied to the fingertip. The solution is colorable, but preferably transparent.

Further, the present invention can be applied to a system for taking images other than the fingerprint image. If articles which are subject of inspection have uneven surfaces, images of uneven pattern on the surfaces can be taken easily according to the present invention.

As described above, according to the present invention, a solution of an electron-donating dye precursor (color former) is applied to a fingerprint face of a fingertip and a recording film is pressed with the fingertip so that a fingerprint image can be generated or produced and recorded. Accordingly, the solution of the electron-donating dye precursor which adheres to the fingertip is put into contact with an electron-accepting color developer so that a coloring reaction occurs instantly, thereby obtaining a clear fingerprint image.

Since the coloring reaction of the electron-donating dye precursor to the electron-accepting color developer occurs substantially at a moment, an unblurred fingerprint image can be obtained even when performing improper operation such as to rotate the fingertip while contacting with the surface applying the electron-accepting color developer thereto. Also, the fingerprint image generated due to the coloring reaction dose not need drying after taking the fingerprint differently from the conventional system using seal ink, and this makes it possible to make office work efficiently.

On the other hand, a small amount of solution in which the electron-donating dye precursor is dissolved adheres to the fingertip such as not to show a remarkable dirt in general, so that the fingertip does not need wiping or can be wiped easily after taking the fingerprint. Therefore, incidental work to the fingerprint taking process is not required or remarkably simplified.

If the solution of the electron-donating dye precursor is microencapsulated so that the microcapsules containing the solution therein can be ruptured merely by pressing them lightly with a finger, the amount of the solution to be applied to the fingertip are easily controlled, thereby obtaining desired handling easily.

In the above case, the microcapsules are preferably ruptured under pressure of approximately 0.2 to 0.6 MPa. Also, the amount of the solution to be applied to the fingertip, the solution containing the electron-donating dye precursor, is set preferably so that the amount of the solution to be transferred from the fingertip to a recording film falls in a range of 20 to 100 $\mu g/cm^2$.

A fingerprint image recording sheet practically used to carry out such methods includes a fingerprint image recording portion formed by applying an electron-accepting color developer to a recording paper, and an electron-donating dye precursor applied portion. In such a recording sheet, if the electron-donating dye precursor is microencapsulated, the amount of the electron-donating dye precursor to be applied to the fingertip is easily controlled and desired handling is obtained.

The fingerprint image recording portion and the electron-donating dye precursor applied portion are formed in different regions adjacent to each other, so that the fingertip is rubbed against one region and pressed against adjacent region, thus making handling remarkably easy. Further, the fingerprint image recording portion can be covered with a light-shielding film capable of opening and closing, so that the electron-accepting color developer can be prevented from changing or losing color, and this makes it possible to improve long-range preservative property of the recorded fingerprint image.

If the fingerprint image recording portion is covered with a removable film and the electron-donating dye precursor applied portion is formed on the upper face of the removable film, a document recording region of the recording sheet will be enlarged, thus obtaining a small sized recording sheet. In this case, the film is torn off after rubbing the upper face of the film with a fingertip so as to apply the electron-donating dye precursor to the fingertip. Then, the fingertip is pressed against the fingerprint image recording portion exposed after removing the film, thus generating the fingerprint image easily. Alternatively, the film used herein may be a light-shielding film with which the fingerprint image recording portion is covered after recording the fingerprint on the fingerprint image recording portion, the light-shielding film does not need preparing separately, and this is convenient to handle.

What is claimed is:

1. A fingerprint image generating method comprising:

micro-encapsulating a solution of an electron-donating dye precursor to form microcapsules containing the solution;

applying the microcapsules to a support to form a micro-encapsulated layer on the support;

rubbing the micro-encapsulated layer with a fingerprint face of a fingertip so that the solution of the electron-donating dye can be applied to the fingerprint face of the fingertip; and pressing the fingertip against a recording film to which an electron-accepting color developer is applied, so that the electron-donating dye precursor is adsorbed by the electron-accepting color developer to cause a coloring reaction therebetween on the recording film;

wherein the solution of the electron-donating dye precursor is present in an amount such that from 20 to 100 $\mu$g $cm^2$ of the solution is transferred from the fingerprint face to the recording film.

* * * * *

UNITED STATES PATENT AND TRADEMARK OFFICE
CERTIFICATE OF CORRECTION

PATENT NO. : 5,811,366
DATED : September 22, 1998
INVENTOR(S) : NOZOMU CHIKAMI

It is certified that error appears in the above-identified patent and that said Letters Patent is hereby corrected as shown below:

On the cover page, in item "[73] Assignee:", change "FUJI PHOTO FILM CO., INC., Kanagawa, Japan" to --FUJI PHOTO FILM CO., LTD., Kanagawa, Japan--.

Signed and Sealed this

Eighteenth Day of May, 1999

Attest:

Q. TODD DICKINSON

Attesting Officer    Acting Commissioner of Patents and Trademarks